United States Patent [19]

Lacroix et al.

[11] 4,046,883

[45] Sept. 6, 1977

[54] FUNGICIDAL COMPOSITIONS BASED ON POLYIMIDES OF PHOSPHORUS AND METHOD OF TREATING PLANTS THEREWITH

[75] Inventors: Guy Lacroix, Lyon; Jean-Claude Debourge, Courbevoie, both of France

[73] Assignee: Philagro S.A., France

[21] Appl. No.: 620,377

[22] Filed: Oct. 7, 1975

[30] Foreign Application Priority Data

Oct. 8, 1974 France .............................. 74.34530

[51] Int. Cl.$^2$ .............................................. A01N 9/36
[52] U.S. Cl. ................................... 424/209; 424/220
[58] Field of Search .............................. 424/209, 220

[56] References Cited

PUBLICATIONS

Chemical Abstracts, vol. 76 (1972), p. 143052y.
Chemical Abstracts, vol. 79 (1973), p. 73093y.

*Primary Examiner*—V. D. Turner
*Attorney, Agent, or Firm*—Robert E. Burns; Emmanuel J. Lobato; Bruce L. Adams

[57] ABSTRACT

Fungicidal compositions containing as the active ingredient at least one compound of the formula, $(RN)_6P_4$, wherein R is an alkyl group containing 1 to 4 carbon atoms are disclosed, as well as a method of controlling fungus diseases of plants by applying such compositions.

2 Claims, No Drawings

FUNGICIDAL COMPOSITIONS BASED ON POLYIMIDES OF PHOSPHORUS AND METHOD OF TREATING PLANTS THEREWITH

The present invention is concerned with fungicide compositions which may be used in the control of plant fungal diseases. More especially, it deals with fungicide compositions containing as active material at least one compound of the molecular formula $(R-N)_6P_4$ in which R is an alkyl radical of 1 to 4 carbon atoms and preferably methyl or ethyl.

The methyl derivative is itself known, cf. Holmes (J. Am. Chem. Soc., Vol. 83, p. 1334–1336, 1960). It exists in the form of a white crystalline solid, insoluble in water and soluble in numerous organic solvents. This compound, for which Holmes proposes a "cage" structure, is obtained by the reaction of phosphorous trichloride on methylamine as follows:

$4PCl_3 + 6CH_3NH_2 \rightarrow (CH_3N)_6P_4 + 12HCl$

The reaction proceeds with an increased yield in the presence of an excess of methylamine. This excess requires removal at the end of the reaction by gas elimination with heat. The reaction as such being exothermic, the reaction medium should be cooled.

In practice, the experimental procedure is as follows: 150 cc of monomethylamine are liquefied in a reactor which is held in a refrigerating bath for the whole of the reaction. Under a flow of nitrogen, 55 g (0.4 mole) of $PCl_3$ is run dropwise into the reactor. This is then allowed to come to room temperature during a period of 5 days, after which it is heated for 2 hours at 50° C to drive off the excess monomethylamine. On filtering under nitrogen, a solid mass is obtained. After drying and crushing, this is purified by extraction with petroleum ether. After removal of the solvent, a white precipitate is obtained which is sublimed at 90° C under vacuum (compound 1).

Yield — 67%
M.P. — 119° C
Percentage analysis for $C_6H_{18}N_6P_4$

| % | C | H | N | P |
|---|---|---|---|---|
| Calculated | 24.17 | 6.08 | 28.19 | 41.56 |
| Found | 24.05 | 6.06 | 28.16 | 41.65 |

In the same way, the corresponding ethyl derivative has been prepared (compound 2), starting with 69 g (0.5 mole) of phosphorous trichloride and 300 ml of monoethylamine. After the reaction, the excess ethylamine is eliminated by evaporation at 80° C. The liquid medium solidifies on cooling to room temperature under nitrogen. The extraction with petroleum ether is carried out, and after elimination of the latter, a colorless oil is obtained. The product is taken up in hexane and distilled under vacuum:

B.P. — 120° C/0.05 mm Hg
M.P. — 25°–30° C
Molecular weight determined by cryoscopy in benzene — 382
Percentage analysis for $C_{12}H_{30}N_6P_4$

| % | C | H | N | P |
|---|---|---|---|---|
| Calculated | 37.75 | 7.85 | 22.00 | 32.50 |
| Found | 37.43 | 8.29 | 21.88 | 32.54 |

The NMR spectra of the two compounds obtained agrees with the cage structure proposed in the literature.

The compounds are solid at room temperature, insoluble in water but soluble in numerous common organic solvents. This property is particularly advantageous, as it allows a wide variety in their formulation, and hence a great flexibility of application.

The following examples illustrate the fungicidal properties of these compounds.

EXAMPLE 1

Test in vivo with Plasmopara viticola (phycomycetes) on vine plants a. Preventative treatment Vine plants (Gamay), pot-cultivated, are sprayed on the underside of the leaves with an aqueous suspension of a wettable powder of the following weight composition:
 active material under test — 20%
 deflocculant (calcium lignosulphate — 5%
 wetting agent (sodium alkylarylsulphonate) — 1%
 support (aluminum silicate) — 74%
at the desired dilution, containing the active material under test at the level in question; each test consists of three repetitions.

After 48 hours, contamination is carried by spraying on the underside of the leaves an aqueous suspension of about 80,000 units/cc of fungal spores. The pots are then placed for 48 hours in an incubation cell at 100% relative humidity and 20° C.

The plants are checked 9 days after the infestation. Under these conditions, compounds 1 and 2 may be observed to provide total protection at a level of 0.5 g/l.

It may also be pointed out that neither of the products tested has shown the least phytotoxicity.

b. Treatment after contamination

The same procedure is sued as in paragraph (a), with the difference that the contamination is carried out first, followed by the treatment with the material under test, observation being carried out 9 days after the contamination.

Under these conditions, compound 1 may be seen to halt completely the development of mildew on the vine seedlings, to the level of 1 g/l.

c. Systemic test on vine mildew by root absorption

Several vine plants (Gamay), each in a pot containing vermiculite and a nutritive solution, are watered with 40 cc of a solution of the material under test at 0.5 g/l. After 2 days, the vine is contaminated with an aqueous suspension containing 100,000 spores/cc of Plasmopara viticola. Incubation is subsequently carried out for 48 hours, in conditions of 100% relative humidity and at 20° C. Observations on the degree of infestation take place after about 9 days, comparing with an infested control which has been watered with 40 cc of distilled water.

Under these conditions, compounds 1 and 2 may be observed to provide total protection of the vine leaves against mildew by root absorption, at this level of 0.5 g/l, and hence demonstrating the systemic character of these compounds.

d. Outdoor trial

Groups of vine plants (Gamay) are treated at a level of 200 g/hl every 8 days from July 5 to August 20 with a wettable powder containing 50% active material constituted by compound 1.

Contamination appears naturally, and is kept up during the month of August artificially by spraying. A check is carried out at the end of September by counting the mildew spots per group. Under these conditions, and in spite of considerable attacks of mildew from July to September, total protection is observed of the treated leaves as well as the shoots, thus confirming the preventative and systemic activity observed under glass. Finally, no phytotoxicity has been noticed.

EXAMPLE 2

Trial on melon seedlings with *Colletotrichum lagenarium* (ascomycetes), responsible for melon antrachnosis Melon seedlings (Cantaloup), 8 days old, are treated by spraying with an aqueous suspension of a wettable powder of the same composition as in example 1, and containing 2 g/l of the product under test, onto the topside of the cotyledonous leaves. 48 hours later, a suspension of spores of *Colletotrichum lagenarium* (100,000 spores/ml) is sprayed with a Fisher-type pistol onto the topside of the leaves, and the young plants incubated for 48 hours in a humid environment. Observation is carried out 8 to 10 days later.

Under these conditions, compound 1 may be observed to provide good protection of the seedlings against the fungus.

EXAMPLE 3

Trial in vivo on celery plants with *Septoria apii*, responsible for celery septoriosis Celery plants, Plein Blanc de Paris (Full Paris White) golden variety, cultivated in pots and about 3 months old are used for the trial, at the 4 to 5 leaf stage.

The fungicide treatment is carried out on two occasions 48 hours apart by spraying, with a Fisher-type pistol, the underside of the foliage, each time an aqueous suspension of a wettable powder of the same composition as in example 1, containing 1 g/l of active material. The contamination is effected 24 hours later by spraying the underside of the leaves with a suspension of about 700,000 spores/cc. The pots are then placed in a humid incubation cell for 72 hours. A check on the plants is about 3 weeks after contamination.

For the test to be valid, the two control seedlings must be infested to the extent of at least 75%.

Under these conditions, compound 1 exhibits good protection of the plants against the fungus.

These examples demonstrate the remarkable fungicida properties of the compounds covered by the invention, characterized by an immediate and systemic action on phycomycetes such as vine mildew, and also fungi of other families such as ascomycetes and fungi imperfecti, associated with the absence of phytotoxicity. Interesting results have also been obtained for the control of mildew in tobacco and hops, as well as certain phytophtora.

However, they have also shown themselves highly efficient against other types of parasitic fungus such as: *Peronospora tabacci, Pseudoperonospora humili, Phytophthora cactorum, Phytophthora capsici, Bremia lactucae, Phytophthora infestans, Peronospora sp., Phytophthora palmivora, Phytophthora phaseoli, Phytophthora megasperma, Phytophthora dreschsteri* and other *Phytophthora sp.*, on temperate or tropical cultivations such as: tobacco, hops, market-gardening and especially strawberry, pimento, onion, sweet pepper, tomato, kidneybean, on ornamental plants, and on pineapple, soybean, citrous, cacao, coconut, rubber tree.

These compounds are thus particularly suited for use in preventative or curative treatment of fungal diseases of plants, especially vine mildew.

The compounds covered by the invention may be used to advantage as mixtures with each other or with other known fungicides such as the metallic dithiocarbamates (manebe, zinebe, mancozebe), the basic salts or hydroxides of copper (oxychloride, oxysulphate), the tetrahydrophthalimides (captane, captafol, folpel), methyl N(1-butylcarbamyl) 2-benzimidazole carbamate (benomyl), the 1,2 di-(3-methoxy or -ethoxy) carbonyl-2-thioureidobenzenes (thiophanates), methyl 2-benzimidazole carbamate etc., either to complete the activity spectrum of the compounds covered by the invention, or to increase their persistence.

The applicant has also observed that these compounds may be mixed with other anti-mildew fungicidal phosphorus derivatives, namely the 2-hydroxy 1,3,2-dioxaphospholanes the β-hydroxyethylphosphites, phosphorous acid and its salts, the phosphonic monoesters and their salts, the phosphonic diesters, the cyclic diphosphorus compounds and the aminophosphites, which respectively come under French patent applications Nos. 73-01.803, 73-37.994, 73-43.081, 73-45.627, 71-08.995, 74-10.988, and 74-13.246.

The level of application may vary within wide limits, depending on the virulence of the fungus and the climatic conditions. In general terms, formulations containing between 0.01 and 5 g/l of active material are convenient to use.

In practical terms, the compounds covered by the invention are rarely used alone. More often than not, they are used in compositions which include, in general, a support and/or a surface-active agent, as well as the active material covered by the invention.

The term "support" in the sense of the present description designates a material, organic or inorganic, natural or synthetic, with which the active material is associated, in order to facilitate its applicator onto the plant, on seeds, or on the soil, or its transport or manipulation. The support may be solid (clays, natural or synthetic silicates, resins, waxes, solid fertilizers . . .) or liquid (water, alcohols, ketones, petroleum fractions, clorinated hydrocarbons, liquefied gases).

The surface-active agent may be an emulsifying, dispersive or wetting agent, ionic or non-ionic. For example, polyacrylic acid salts, lignin sulphonic acid salts, condensates of ethylene oxide on fatty alcohols, fatty acids or fatty amines.

The compositions covered by the invention may be prepared in the form of wettable powders, dusting powders, granules, solutions, emulsifiable concentrates, emulsions, concentrates in suspension, and aerosols.

The wettable powders are usually prepared in such a way that they contain from 20 to 95% by weight of material, and usually contain, in addition to the solid support, from 0 to 5% by weight of wetting agent, from 3 to 10% by weight of a dispersive agent, and, when necessary, from 0 to 10% by weight of stabilizer(s)

and/or other additives such as penetrating agents, adhesives, or anti-clumping agents, coloring etc. As an example, the composition of a wettable powder is given below:

- active material — 50%
- calcium lignosulphate (deflocculant) — 5%
- anionic wetting agent — 1%
- silica, anti-clumping agent — 5%
- kaolin (support) — 39%

Aqueous dispersions and emulsions, for example formulations obtained by diluting a wettable powder or an emulsifiable concentrate covered by the invention with water are included in the general framework of the present invention. These emulsions may be of the water-in-oil type or oil-in-water type and may have a thick consistency like that of "mayonnaise".

The formulations covered by the invention may contain other ingredients, for example protective colloids, adhesives or thickeners, thixotropic agents, stabilizers or sequestering agents, as well as other well-known active materials with pesticidal properties, in particular acaricides or insecticides.

We claim:

1. A method of treating plants to control fungal diseases thereof comprising applying to said plants a fungicidally effect amount of at least one compound of the formula $(RN)_6P_4$ in which R is an alkyl radical containing 1 to 4 carbon atoms.

2. A method of treating plants according to claim 1 in which said compound is applied in an agriculturally acceptable composition containing about 0.01 to 5 g. per liter of said compound.

* * * * *